United States Patent [19]

Wegmüller et al.

[11] 4,180,084

[45] Dec. 25, 1979

[54] COSMETIC COMPOSITIONS CONTAINING POLYMERIC QUATERNARY AMMONIUM SALTS

[75] Inventors: Hans Wegmüller, Riehen, Switzerland; Ulrich Horn, Greenville, S.C.; Walter Hungerbühler; Jaroslav Haase, both of Riehen, Switzerland

[73] Assignee: Ciba-Geigy Corporation, Ardsley, N.Y.

[21] Appl. No.: 899,940

[22] Filed: Apr. 25, 1978

[30] Foreign Application Priority Data

May 2, 1977 [CH] Switzerland .................. 5463/77

[51] Int. Cl.$^2$ ............................................. A45D 7/00
[52] U.S. Cl. ............................ 132/7; 424/DIG. 1; 424/DIG. 2; 424/47; 424/70; 424/71
[58] Field of Search ....... 132/7; 424/DIG. 1, DIG. 2, 424/47, 70, 71

[56] References Cited

FOREIGN PATENT DOCUMENTS 2521960 4/1976 Fed. Rep. of Germany ....... 132/7 UX
2657582 7/1977 Fed. Rep. of Germany ....... 132/7 UX

*Primary Examiner*—G. E. McNeill
*Attorney, Agent, or Firm*—Michael W. Glynn

[57] ABSTRACT

Hair-care compositions in the form of aqueous, alcoholic or aqueous alcoholic solutions, creams, gels, emulsions, or of aerosols which optionally contain a propellant are provided which contain at least one polymeric quaternary ammonium salt which contains cationic units of the formula

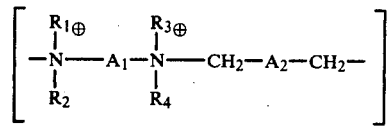

wherein $R_1$, $R_2$, $R_3$ and $R_4$ are the same or different and represent alkyl, cycloalkyl or alkenyl, aryl or aralkyl, or ($R_1$ and $R_2$) and/or ($R_3$ and $R_4$) together with the nitrogen atom to which they are bonded, form an unsubstituted or substituted heterocyclic ring containing 3 to 6 ring members, $A_1$ represents an optionally substituted alkylene, cycloalkylene or aralkylene bridging group and $A_2$ is a group of the formula

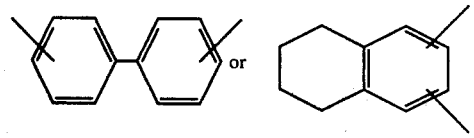

The compositions are especially useful as shampoos.

15 Claims, No Drawings

COSMETIC COMPOSITIONS CONTAINING POLYMERIC QUATERNARY AMMONIUM SALTS

The use of polymeric quaternary ammonium salts in quaternary ammonium salts in cosmetic compositions is known from German Offenlegungsschrift No. 2,521,960. These quaternary ammonium salts contain recurring units of the formula

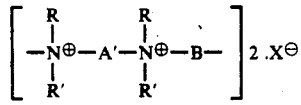

wherein $X^\ominus$ is an anion of a mineral acid or of an organic acid, R is lower alkyl or hydroxyethyl and R' is an aliphatic, cycloaliphatic or araliphatic radical containing not more than 20 carbon atoms, or R and R' together with the nitrogen atom to which they are bonded can form a heterocyclic ring system which, in addition to the nitrogen atom, can also contain a further heteroatom, and A' and B are the group

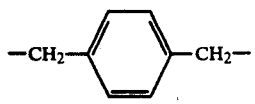

or aliphatic groups, unsubstituted or substituted groups or groups which are interrupted by heteroatoms, but no mention is made of the bridge members

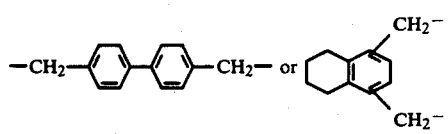

either as A' or as B.

Cosmetic compositions, especially hair-care preparations, which contain these quaternary ammonium salts are not entirely satisfactory in all repects. If the quaternary ammonium salts are used, for example, in hair setting aids, the resulting hairstyle is of poor stability and, especially in a moist climate, rapidly loses its shape.

It is the object of the present invention to provide new cosmetic compositions, especially hair-care compositions, which result in an improved stability of the hairstyles for which they are used.

Accordingly, the present invention relates to the use of polymeric quaternary ammonium salts which contain cationic units of the formula

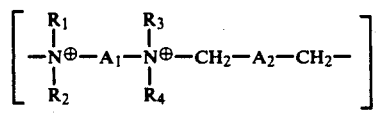

(1)

wherein $R_1$, $R_2$, $R_3$ and $R_4$ are the same or different and represent unsubstituted or substituted alkyl, cycloalkyl or alkenyl of at most 20 carbon atoms, aryl or aralkyl, or ($R_1$ and $R_2$) and/or ($R_3$ and $R_4$) together with the nitrogen atom to which they are bonded, form an unsubstituted or substituted heterocyclic ring containing 3 to 6 ring members, $A_1$: represents $-(CH_2)_m$, wherein m is an integer from 1 to 20, which can be interrupted by at least one $-S-$,

or $-CH=CH-$ group or substituted by at least one member selected from the group consisting of hydroxyl, halogen, nitrile, alkyl, hydroxyalkyl, alkoxy, carboxyl or carbalkoxy or by at least one unsubstituted or substituted aryl or aralkyl radical, or represents polyoxyalkylene, or a radical of the formulae

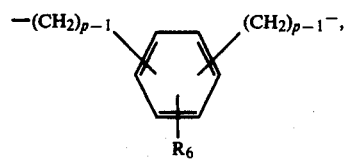

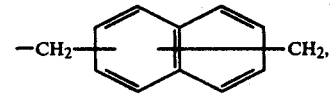

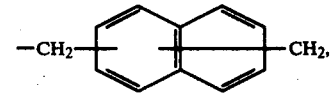

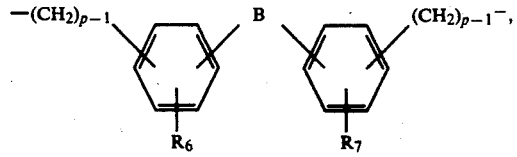

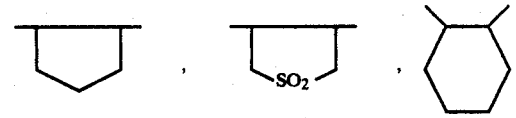

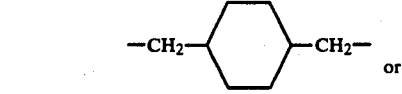

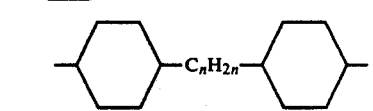

or together with the nitrogen atoms and at least one of the substituents bonded thereto represents a radical of the formulae

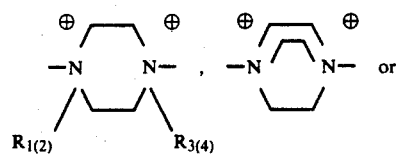

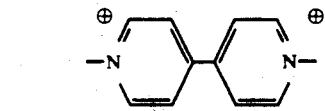

$R_6$ and $R_7$: represent hydrogen, alkyl, hydroxyl or haloalkyl of 1 to 4 carbon atoms, hydroxyl, halogen, carboxyl, carbalkoxy or phenyl, B represents the direct bond, —O—,

—S—, —SO$_2$— or unsubstituted or substituted alkylene, n is an integer from 1 to 6, p is an integer from 1 to 3, preferably 1 to 2, and $A_2$ represents a radical of the formula

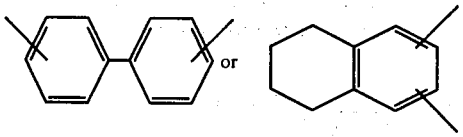

in cosmetic compositions.

The invention also relates to the cosmetic compositions themselves and also to cosmetic methods of treatment which comprises the use of the compositions.

The radicals $R_1$, $R_2$, $R_3$ and $R_4$ in the cationic units of the polymeric quaternary ammonium salts of the formula (1) can be straight-chain or branched alkyl radicals of 1 to 20 carbon atoms, for example methyl, ethyl, propyl, isopropyl, butyl, isobutyl, tert-butyl, hexyl, octyl, isooctyl, tert-octyl, decyl, dodecyl, tetradecyl, hexadecyl, octadecyl or eicosyl.

Preferred radicals are alkyl radicals of 1 to 10, especially 1 to 4, carbon atoms. Methyl and ethyl are particularly preferred.

Substituted alkyl radicals are for example hydroxyalkyl, cyanoalkyl, alkoxyalkyl, alkylthioalkyl, alkylcarbonylalkyl, alkyl, sulphonylalkyl, arylcarbonylalkyl and arylsulphonylalkyl, wherein aryl is a mono-, bi- or trinuclear aromatic hydrocarbon, especially phenyl or naphthyl: alkylcarboxylic acid, carbalkoxy and dicarbalkoxyalkyl; carboxamidoalkyl which can be N- or N,N-substituted by lower ($C_1$-$C_4$) alkyl or aryl, for example phenyl.

The cycloalkyl radicals are in particular cyclopentyl and cyclohexyl which can be unsubstituted or substituted.

The alkenyl radicals can contain 2 to 20 carbon atoms and those containing 2 to 10 or, in particular, 2 to 4, carbon atoms are preferred. Suitable alkenyl radicals are those corresponding to the cited alkyl radicals. The substituents of the alkyl radicals can in general also be substituents of the alkenyl radicals.

Aryl and aralkyl radicals are in particular phenyl and benzyl which are unsubstituted or substituted by hydroxyl, cyano, halogen (fluorine, chlorine, bromine, iodine), carboxyl; alkyl, hydroxyalkyl, cyanoalkyl, alkoxy and alkylthio, the preferred radicals being lower alkyl and alkoxy; alkoxyalkyl, carbalkoxyalkyl and dicarbalkoxyalkyl, the alkyl and alkoxy moieties of which contain preferably 1 to 4 carbon atoms; alkylcarboxylic acid, wherein alkyl preferably contains 1 to 4 carbon atoms; carboxamidoalkyl which can be N- or N,N-substituted by lower ($C_1$-$C_4$)alkyl.

The two substituents at each nitrogen atom, together with the nitrogen atom to which they are bonded, can furthermore form an unsubstituted or substituted heterocyclic ring containing 5 or 6 ring members. Such rings are for example the piperidine, morpholine, thiomorpholine, pyrrolidine or imidazoline ring.

The bridge member $A_1$ is for example an alkylene group of the formula —(CH$_2$)$_m$—, wherein m is an integer from 1 to 20, preferably 1 to 12. The alkylene group can be interrupted by a sulphur atom or by

or —CH=CH—, optionally there are more than one of these groups present. Possible substituents which are bound to the alkylene chain can be hydroxyl, halogen, especially fluorine, chlorine and bromine, nitrile, alkyl, hydroxyalkyl or alkoxy of preferably 1 to 4 carbon atoms, for example methyl, ethyl, propyl, isopropyl and butyl, hydroxymethyl or hydroxyethyl or methoxy, ethoxy, propoxy, and butoxy, also carboxyl (—COOH) and carbalkoxy of 1 to 20 carbon atoms.

Further substituents can be aryl and aralkyl, preferably phenyl and benzyl, which can be further substituted by lower alkyl, halogen or hydoxyl.

A polyoxyalkylene radical represented by the bridge member $A_1$ is primarily a polyoxyethylene or especially polyoxypropylene radical: —(CH$_2$CH$_2$O)$_x$CH$_2$CH$_2$— or

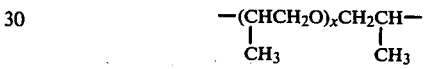

wherein x is at least 1. The maximum limit for x can be about 50, whilst preferred values are between about 1 and 40, preferably between 4 and 40.

$A_1$ can also be an aromatic bridge member which is derived from mono- or binuclear aromatics (benzene, naphthalene). Examples are unsubstituted or substituted phenylene which is bonded to the nitrogen atom through methylene groups (—CH$_2$—); substituted naphthalene, unsubstituted or substituted diphenyl, diphenyl oxide, diphenyl sulphide, diphenyl sulphone or benzophenone. The possible substituents at these aromatic bridge members are usually lower alkyl, lower hydroxyalkyl or haloalkyl of 1 to 4 carbon atoms, hydroxyl, halogen, especially chlorine and bromine, carboxyl, carbalkoxy and phenyl.

Bridge members containing cycloalkyl groups are in particular groups of the formulae

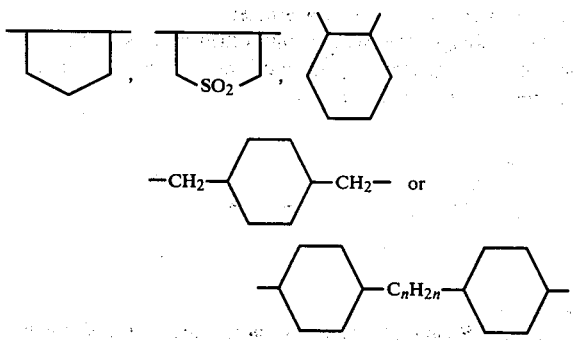

wherein n is an integer from 1 to 6.

The bridging between the two nitrogen atoms can also be effected through the substituents ($R_1$-$R_4$) which are linked to these atoms. Including the two nitrogen atoms, piperazine, 1,4-diazabicyclo-(2,2,2)octane or dipyridyl groups are then obtained for example.

Particularly suitable polymeric quaternary ammonium salts contain the cationic units of the formula

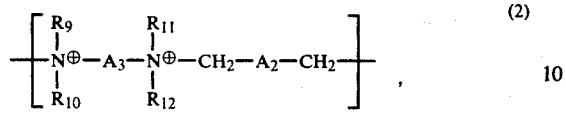
(2)

wherein $R_9$, $R_{10}$, $R_{11}$ and $R_{12}$ are the same or different and represent alkenyl of 2 to 20 carbon atoms, cycloalkyl of 5 to 6 carbon atoms; alkyl, hydroxyalkyl, cyanoalkyl, alkoxyalkyl, alkylthioalkyl and alkylcarbonylalkyl of 1 to 10 carbon atoms; arylcarbonylalkyl, alkylsulphonylalkyl and arylsulphonylalkyl, each containing 1 to 4 carbon atoms in the alkyl moiety; alkylcarboxylic acid containing 1 to 4 carbon atoms in the alkyl moiety; carbalkoxyalkyl and di(carbalkoxy)alkyl, each containing 1 to 4 carbon atoms in the alkoxy and alkyl moieties; carboxamidoalkyl containing 1 to 10 carbon atoms in the alkyl moiety and which can be N-substituted by lower alkyl or aryl; or represent phenyl or benzyl which are unsubstituted or substituted by hydroxyl, cyano, halogen and carboxyl; alkyl, hydroxyalkyl, cyanoalkyl, alkoxy and alkylthio of 1 to 4 carbon atoms; alkoxyalkyl, carbalkoxyalkyl and di(carbalkoxy)alkyl, each containing 1 to 4 carbon atoms in the alkyl and alkoxy moieties; alkylcarboxylic acid containing 1 to 4 carbon atoms in the alkyl moiety; or carboxamidoalkyl containing 1 to 4 carbon atoms in the alkyl moiety and which is unsubstituted or N-substituted by lower alkyl; or ($R_9$ and $R_{10}$) and/or ($R_{11}$ and $R_{12}$), together with the nitrogen atom to which they are bonded, form an unsubstituted or substituted heterocyclic ring containing 5 to 6 ring members, $A_3$ represents —(CH$_2$)$_m$—, wherein m is an integer from 1 to 20, which can be interrupted by at least one —S—,

or —CH=CH— group or substituted by at least one member selected from the group consisting of hydroxyl, chlorine, nitrile or alkyl, alkoxy or hydroxyalkyl of 1 to 4 carbon atoms, carboxyl or carbalkoxy containing 1 to 20, preferably 1 to 4, carbon atoms in the alkoxy moiety, or by unsubstituted or substituted phenyl or benzyl radicals; or also represents a group of the formula

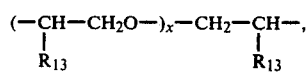

a radical of the formulae

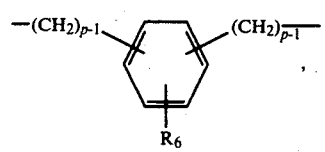

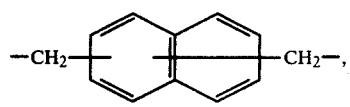

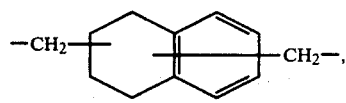

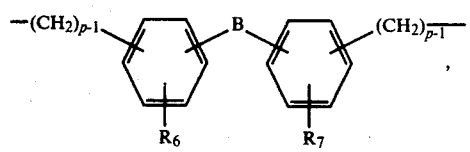

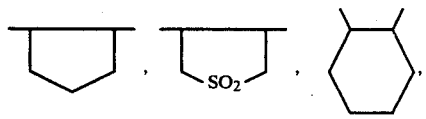

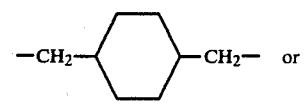

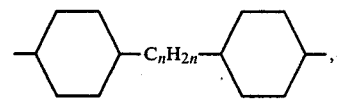

or together with the nitrogen atoms and at least one of the substituents which are bonded thereto is a radical of the formulae

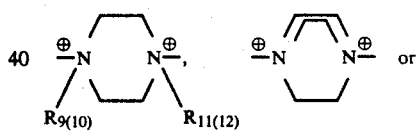

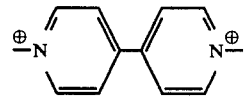

$R_{13}$ represents hydrogen or methyl and x is at least 1, and $A_2$, $R_6$, $R_7$, B, n and p have the meanings previously given.

Those polymeric quaternary ammonium salts are also preferred which contain cationic units of the formula

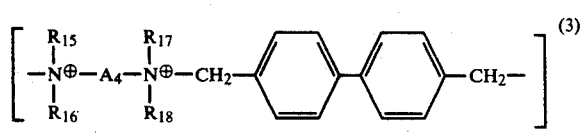
(3)

wherein
$R_{15}$, $R_{16}$, $R_{17}$ and $R_{18}$ are the same or different and represent alkyl, hydroxyalkyl, alkoxyalkyl, alkylthioalkyl and cyanoalkyl of 1 to 4 carbon atoms; cyclopentyl, cyclohexyl, alkenyl of 2 to 4 carbon atoms, CH$_3$COCH$_2$—, HOOC—CH$_2$—, CH$_3$OOCCH$_2$—, H$_5$C$_2$OOCCH$_2$—, (CH$_3$OOC)$_2$CH—, H$_2$NCOCH$_2$—,

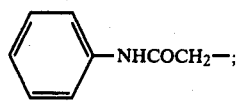

or represent phenyl or benzyl which are unsubstituted or substituted by hydroxyl, amino, cyano, fluorine, chlorine, bromine, alkyl, hydroxyalkyl, cyanoalkyl, alkoxy and alkylthio, each containing 1 or 2 carbon atoms, alkoxyalkyl, carbalkoxyalkyl and di(carboxyalkyl) containing 1 or 2 carbon atoms in the alkyl and alkoxy moiety —CH$_2$COOH, —(CH$_2$)$_2$COOH, carboxamidoalkyl with 1 or 2 carbon atoms on the alkyl moiety and optionally N-substituted by lower alkyl, or (R$_{15}$ and R$_{16}$) and/or (R$_{17}$ and R$_{18}$) together with the nitrogen atom to which they are bonded form a heterocyclic ring of the formulae

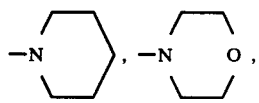

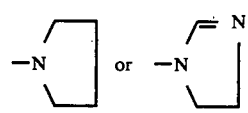

and

A$_4$ represents —(CH$_2$)$_{m_1}$, wherein m$_1$ is an integer from 1 to 12,

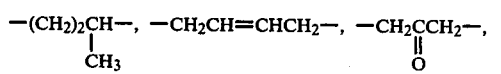

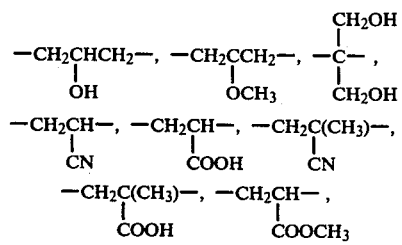

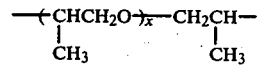

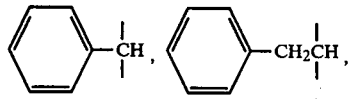

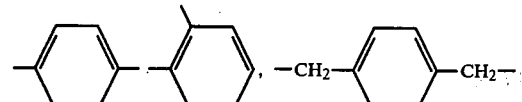

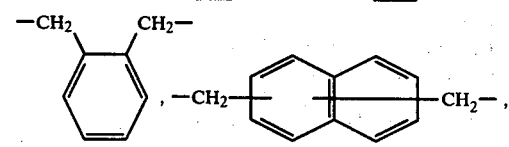

-continued

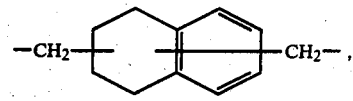

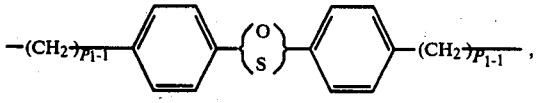

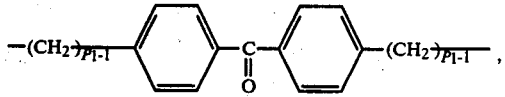

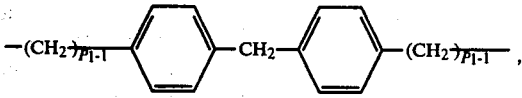

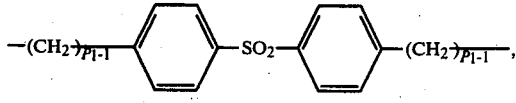

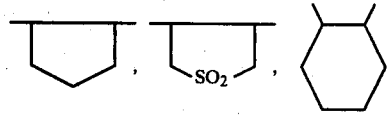

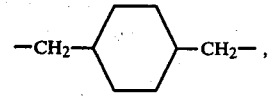

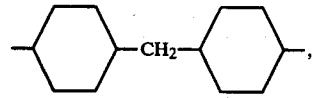

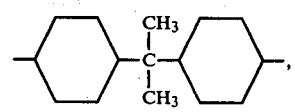

wherein x is at least 1 and p$_1$ is 1 or 2, or together with the nitrogen atoms and at least one of the substituents bonded thereto A$_4$ represents a radical of the formulae

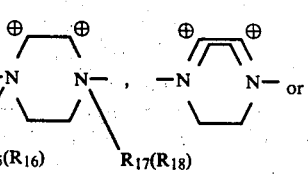

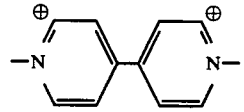

In the cosmetic compositions of the present invention there are used in particular compounds of the formula (3), in which R$_{15}$, R$_{16}$, R$_{17}$ and R$_{18}$ are the same or different and represent alkyl or hydroxyalkyl of 1 to 4 carbon atoms, alkenyl of 2 to 4 carbon atoms, CH$_3$OOCCH$_2$—, C$_2$H$_5$OOCCH$_2$— or benzyl, or (R$_{15}$ and R$_{16}$) and/or (R$_{17}$ and R$_{18}$) together with the nitrogen atom to which they are bonded form a heterocyclic ring of the formula $$-N\bigcirc \quad \text{or} \quad -N\bigcirc O$$

and $A_4$ represents $-(CH_2)_{m1}-$, wherein $m_1$ is an integer from 1 to 12, $$-(CH_2)_2CH-,\ -CH_2CH=CHCH_2-,\ -CH_2CCH_2-,$$
$$\quad\ \ |\qquad\qquad\qquad\qquad\qquad\qquad\qquad\ \ \|$$
$$\quad\ \ CH_3\qquad\qquad\qquad\qquad\qquad\qquad\ \ O$$
$$-CH_2-CH-CH_2-,\ \ \ (CH-CH_2-O)_x-CH_2-CH-,$$
$$\qquad\quad\ |\qquad\qquad\qquad\ \ |\qquad\qquad\qquad\qquad |$$
$$\qquad\quad OH\qquad\qquad\qquad CH_3\qquad\qquad\qquad\quad CH_3$$

wherein x is at least 1,

[structures: $-CH_2-C_6H_4-CH_2-$, naphthalene diyl, decahydronaphthalene diyl, o-xylylene, $-CH_2-C_6H_4-C_6H_4-CH_2-$, $-CH_2-C_6H_4-O-C_6H_4-CH_2-$, diphenylmethane diyl, diphenylsulfone diyl $-SO_2-$, dicyclohexyl-$C(CH_3)_2$-diyl]

or together with the nitrogen atoms and at least one of the substituents bonded thereto represents a radical of the formulae

[piperazine-based structures with $CH_2COOCH_3$ substituents, $CH_2COOC_2H_5$ substituents, and bipyridyl structure]

Preferred is the use of polymeric quaternary ammonium salts are those in which $A_4$ is $$-(CH_2)_{3-6},\ -(CH(CH_3)CH_2O)_{2,6}CH_2CH(CH_3)-$$

[o-xylylene structure], [dicyclohexyl-$C(CH_3)_2$ structure]

or together with the nitrogen atoms and both substituents bonded thereto is the radical of the formula

[4,4'-bipyridinium structure]

The cationic units of the formula (3) and of the formulae given hereinafter can be isomers or mixtures of isomers, as the diphenyl radical can be substituted by the methylene ($-CH_2-$) groups in different positions. To save the trouble of enumerating all the isomers each time, only the p,p'-substituted isomers will be specifically referred to.

In particular, polymeric ammonium salts containing recurring units of the following formulae are cited by way of example:

$$\left[\begin{array}{c} CH_3\qquad\quad CH_3 \\ |\qquad\qquad\quad | \\ -N^{\oplus}-(CH_2)_{m1}-N^{\oplus}-CH_2-\!\!\bigcirc\!\!-\!\!\bigcirc\!\!-CH_2- \\ |\qquad\qquad\quad | \\ CH_3\qquad\quad CH_3 \end{array}\right]\ 2\ X^{\ominus} \quad (4)$$

wherein $m_1$ is 1 to 12, preferably 3 to 6, and X is halogen.

$$\left[\begin{array}{c} CH_3\qquad\quad CH_3 \\ |\qquad\qquad\quad | \\ -N^{\oplus}-(CH_2)_3-N^{\oplus}-CH_2-\!\!\bigcirc\!\!-\!\!\bigcirc\!\!-CH_2- \\ |\qquad\qquad\quad | \\ CH_3\qquad\quad CH_3 \end{array}\right]\ 2\ Cl^{\ominus} \quad (5)$$

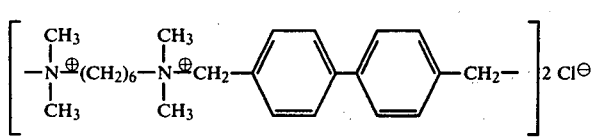
(6)
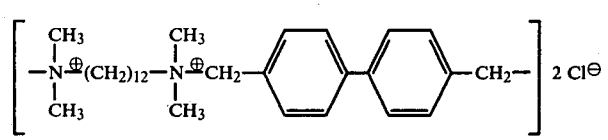
(7)
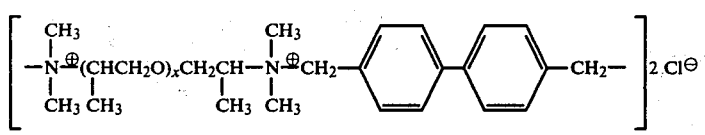
(8)
wherein x is at least 1;
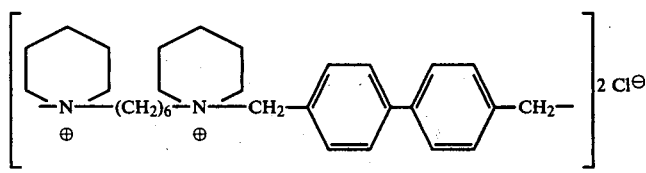
(9)
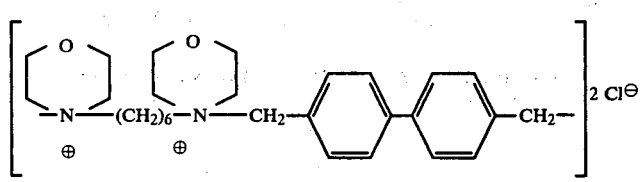
(10)
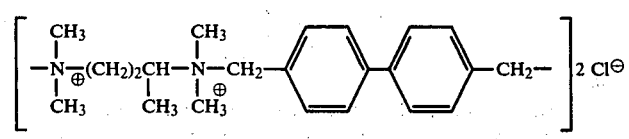
(11)
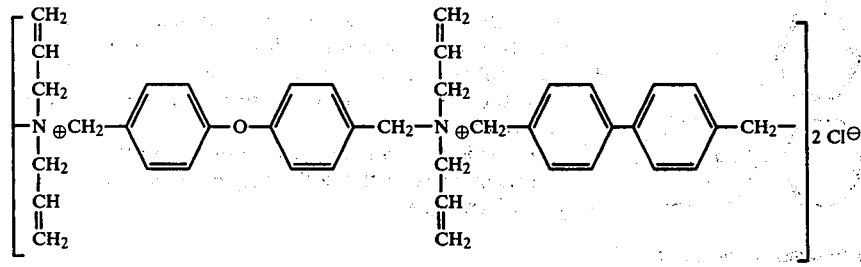
(12)
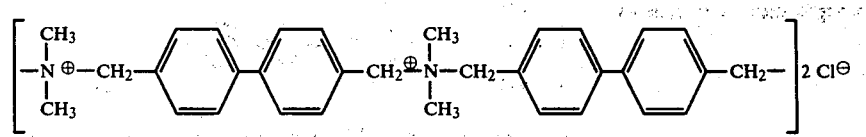
(13)
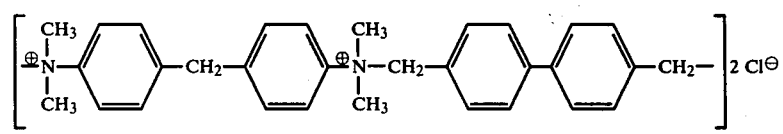
(14)
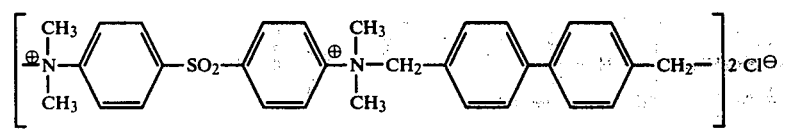
(15)

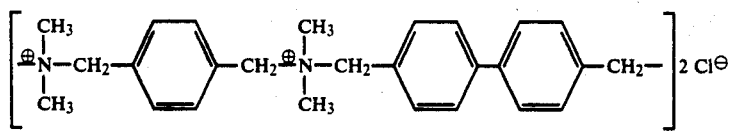
(16)

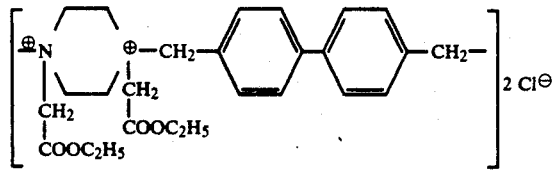
(17)

The compound of the formula (17) is obtained for example by reaction of piperazine with 4,4'-(bischloromethyl)-diphenyl and subsequent quaternisation with ethyl chloroacetate.

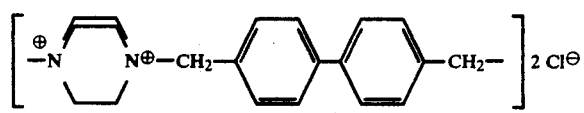
(18)

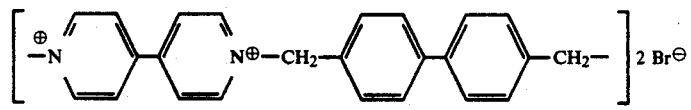
(19)

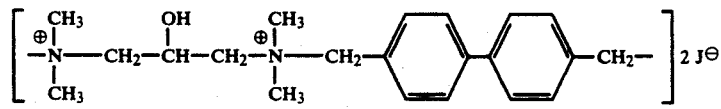
(20)

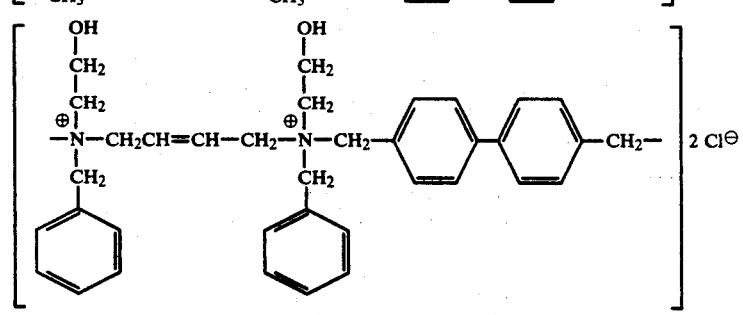
(21)

Suitable anions for the polymeric quaternary ammonium salts of the present invention are all customary inorganic or organic anions which do not form any sparingly soluble complexes with the cations, for the ammonium salts should preferably be water-soluble. They are also generally soluble in alcohols, especially in ethanol and in alcohol/water mixtures. The anions of mineral acids or of low molecular organic acids may be mentioned for example. Suitable anions are for example the halogen anions, such as $I^\ominus$, $Br^\ominus$ and especially $Cl^\ominus$ or methyl sulphate ($CH_3SO_4^\ominus$), ethyl sulphate ($C_2H_5SO_4^\ominus$) and toluene sulphonate or nitrate and sulphate.

The polymeric quaternary ammonium salts can have molecular weights of 400 or 500 to 50,000, preferably up to 25,000 and in particular from about 1500 to about 20,000.

The polymeric quaternary ammonium salts are known compounds. They can be obtained by known methods by reacting for example diamines with dihalogeno compounds in molar ratios of about 1:2 to 2:1, preferably in equimolar amounts (cf. for example German Offenlegungsschrift No. 2,657,582).

The ammonium salts are usually obtained as mixtures and not as pure compounds. The indicated molecular weights can therefore only be regarded as average values.

The polymeric quaternary ammonium salts of the formula (1) have interesting cosmetic properties if they are used in cosmetic compositions which are applied to the hair or skin. The present invention also relates to cosmetic compositions which contain the ammonium salts of the formula (1). These compositions generally contain in addition at least one adjunct which is customarily employed in cosmetic compositions. They can contain the ammonium salts of the formula (1) either as active main component or as ingredient.

These cosmetic compositions can be used in the form of aqueous, alcoholic or aqueous-alcoholic solutions, in which case lower alcohols, such as ethanol or isopropanol, are used, or of emulsions. They can also be in the form of creams, gels, powders, tablets, as well as aerosols which additionally contain a propellant. The compositions can moreover also contain further adjuncts conventionally used in the art of cosmetics formulation, for example perfumes, dyes, solvents, dulling agents and nacreous lustre, for example esters of fatty acids with polyols, magnesium and zinc salts of fatty acids or dispersions based on copolymers; thickening agents, plant extracts, protein derivatives, such as gelatin, collagen hydrolysates, polypeptides on a natural and synthetic basis, lecithin, lanoline and lanoline derivatives, fats, oils, fatty alcohols, silicones, deodorants, antimicrobial substances and chelating agents.

The cosmetic compositions of the present invention can be in the form both of ready-to-use compositions and of concentrates which must be diluted before use.

In general, the concentration of polymeric quaternary ammonium salts of the formula (1) in the cosmetic compositions is preferably between 0.5 to 5% by weight, especially between 0.5 and 1.5% by weight.

The polymeric quaternary ammonium salts of the formula (1) are suitably used according to the present invention in particular for hair-care preparations, preferably shampoos. Examples of further hair-care compositions are hair rinses, hair-restoratives, hair tints, hair lacquers, pre-shampoo hair conditioners, hair tonics, setting lotions, hairsprays, hair creams, hair gels, hair oils, hair pomades or brilliantines.

If the cosmetic compositions are formulated to shampoos, they contain at least one surfactant. Suitable surfactants can be anionic, cationic, non-ionic and amphoteric compounds. Cationic or nonionic compounds are preferred.

Examples of anionic surfactants are: alkyl- and alkylenecarboxylates, alkyl ether carboxylates, fatty alcohol sulphates, fatty alcohol ether sulphates, alkylolamide sulphates and sulphonates, fatty acid alkylolamide polyglycol ether sulphates, alkylphenol glycol ether sulphates, hemiesters and diesters of sulphosuccinic acid or fatty alcohol ether phosphates, wherein the fatty acid or alkyl radicals contain in general 8 to 24 carbon atoms.

These compounds and mixtures thereof are used in the form of their water-soluble or water-dispersible salts, for example in the form of the sodium, potassium, magnesium, ammonium, mono-, di- and triethanolamine salts as well as analogous alkylolammonium salts.

Examples of cationic surfactants are quaternary ammonium salts, such as dialkyldimethylammonium chloride or bromide, alkyl dimethylethylammonium chloride or bromide, alkyl trimethylammonium chloride or bromide, alkyl dimethylbenzylammonium chloride or bromide, N-alkyl pyridinium chloride or bromide, salts of N,N-diethylaminoethyl stearylamide and oleylamide with hydrochloric acid, acetic acid, phosphoric acid, and N-acylamidoethyl-N,N-diethyl-N-benzylammonium chloride, bromide or monoalkylsulphate, wherein acyl represents preferably the radicals of stearic or oleic acid.

Suitable non-ionic surfactants which can be used as detergents in the shampoo are for example: fatty alcohol ethoxylates, alkylphenol polyethylene glycols, alkylamino polyethylene glycols, fatty acid ethoxylates, polypropylene glycol ethoxylates, fatty acid amidopolyethylene glycols, sucrose esters or sorbitan esters.

Amphoteric surfactants are betains, such as N-acylamidoalkyl-N,N-dimethylacetobetain, preferably N-acylaminopropyl-N,N-dimethylacetobetain or alkyldimethylsulphopropylbetain (alkyl containing 12 to 18 carbon atoms); amphoteric surfactants based on imidazoline, preferably the sodium salt of 1-($\beta$-carboxymethyloxyethyl)-1-(carboxymethyl)-2-laurylimidazolinium; amine oxides, for example alkyl dimethylamine oxides (alkyl containing 12 to 18 carbon atoms).

The hair-care compositions in the form of shampoos can additionally contain for example perfumes, dyes, preservatives, thickening agents, foam stabilisers, plasticisers or a cosmetic resin.

Human hair which is washed with a shampoo containing the polymeric quaternary ammonium salts of the formula (1) and subsequently dried, can, on the one hand, be very easily combed when wet and, on the other, can be wound on rollers direct, that is to say without using a setting aid, and then dried in the air or with a hand-drier. After taking out the rollers, the hair can be easily combed, it has fullness and lustre, and the resulting hairstyle has very good retention of shape, especially in a moist climate.

The method of treatment comprises applying the compositions (shampoos) at physiologically tolerable temperatures (20° to 45° C., preferably 40° C.) to the hair, allowing them to act on the hair for $\frac{1}{2}$ minute to 5 minutes, then washing off the compositions at the given temperatures (20° to 45°), winding the hair on rollers to form curls, and drying it at temperatures from about 20° to 60° C. The amount of shampoo used is in general two times 5 to 10 ml per head of hair.

The shampoos have in consequence a double action to the extent that they clean the hair on the one hand and furthermore impart to the hair properties which enable it to be set without having to use a special setting aid, i.e. they are employed as "setting shampoos".

Water wave lotions are suitable for use as hair care preparations, especially for sensitive hair, and contain at least one polymeric quaternary ammonium salt of the formula (1), usually in aqueous, alcoholic or aqueous-alcoholic solution. They can furthermore contain one or more cosmetic resins, especially homopolymers or vinyl copolymers, for example polyvinyl pyrrolidone, the copolymers of polyvinyl pyrrolidone and vinyl acetate, copolymers of crotonic acid and vinyl acetate or cellulose ethers containing quaternary nitrogen atoms, for example those known from U.S. Pat. No. 3,472,840.

The pH of these water wave lotions is generally between 4.5 and 7.5. If desired or necessary, the pH value can be altered, for example by using an alkanolamine, such as monoethanolamine or triethanolamine.

Hair-tints usually contain an adjunct in addition to the polymeric quaternary ammonium salts of the formula (1). The adjunct is preferably so chosen that a cream or gel is obtained.

For an oxidation tinting, the tint can be in two parts, the second of which is hydrogen peroxide. Both parts are mixed before application. Compositions formulated to hair lacquers are generally in the form of an alcoholic or aqueous-alcoholic solution of a resin which is conventionally employed for lacquers and at least one polymeric quaternary ammonium salt of the formula (1). The hair lacquer is normally applied from an aerosol bomb with the aid of a propellant.

Pre-shampoo hair conditioners, which are in the form of aqueous or aqueous-alcoholic solutions, optionally in aerosol containers, or of creams or gels, can be applied before shampooing, especially before shampooing with an anionic and/or non-ionic shampoo, before an oxidation tinting followed by a shampooing with an anionic and/or non-ionic shampoo, or also before a permanent wave treatment.

The polymeric quaternary ammonium salt of the formula (1) is the active constituent in these pre-shampoo hair conditioners and its concentration varies in general between 0.1 and 10% by weight, especially between 0.2 and 5% by weight. The pH value of these compositions varies in general between about 3 and 9.

The cosmetic compositions for the skin are for example in the form of creams, gels, emulsions, or aqueous, alcoholic or aqueous-alcoholic solutions. The further ingredients contained in these cosmetic compositions are for example perfumes, dyes, preservatives, chelating agents, emulsifiers and thickeners.

These compositions for the skin are in particular creams or lotions for the care of the hands or face, sunscreen creams, tinted creams, foaming oils or fluids for adding to baths, or also deodorant preparations. They are prepared by conventional methods.

To obtain a cream for example, it is possible to emulsify a liquid phase containing the polymer and optionally other ingredients and an oily phase. The oily phase can consist of different products, for example paraffin oil, vaseline oil, olive oil, fatty acid esters, such as glycerol monostearate, ethyl or isopropyl palmitates, alkyl myristates, such as propyl, butyl or cetyl myristate. In addition, fatty alcohols, such as cetyl alcohol, or waxes, for example beeswax, can be added.

The cosmetic compositions can contain the polymers of the present invention either as additives or as active main constituents in creams or lotions for the care of the hands or face, or also as additives in sunscreen creams, tinted creams, make-up milk or foaming fluids for adding to baths.

The invention is illustrated by the following Examples, in which the parts and percentages are by weight unless otherwise indicated.

MANUFACTURING DIRECTION 1

(a) 109 g (0.435 mole) of 4,4'-bis-(chloromethyl)-diphenyl and 111 g (0.435 mole) of N,N,N',N'-tetramethyl-1,12-diaminododecane are heated in 440 ml of methanol for 24 hours to reflux temperature.

The solvent is then distilled off and the residue is dried at 40° C. The reaction product dissolves in water to give a clear solution. Yield: 220 g (100% of theory) of a reaction product containing recurring units of the formula

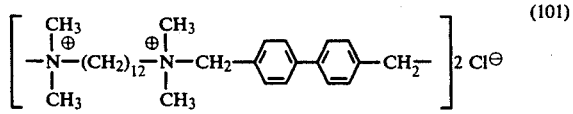

(b) A second batch with the same reactants yields a reaction product with a viscosity of $\eta=0.52$ (25° C. in methanol, [dl/g]) and an average molecular weight of 7600.

(c) A third batch using the same reactants (molar ratio of diamine to dihalide 2:1) yields a reaction product with a viscosity of $\eta=0.10$ (25° C. in methanol, [dl/gl]) and an average molecular weight of 1500.

Reaction products containing recurring units of the general formula

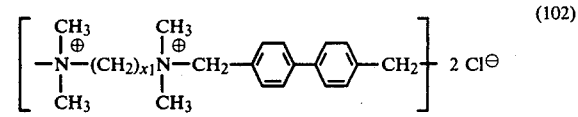

are also obtained in quantitative yield by analogous reaction of 4,4'-bis-(chloromethyl)-diphenyl with N,N,N',N'-tetramethyl-substituted ethylene diamine, 1,3-diaminopropane, 1,4-diaminobutane, 1,6-diaminohexane, 1,8-diaminooctane and 1,10-diaminodecane.

Table I indicates the values for $x_1$, the viscosity and the average molecular weight.

Table I

| Example | $x_1$ | 25° C., methanol [dl/g] | average mol. wt. |
| --- | --- | --- | --- |
| 1 d | 2 | 0.09 | 1300 |
| 1 e | 3 | 0.40 | 5900 |
| 1 f | 4 | 1.26 | 19000 |
| 1 g | 6 | 1.35 | 19800 |
| 1 h | 8 | 0.44 | 6500 |
| 1 i | 10 | 0.46 | 6600 |

MANUFACTURING DIRECTION 2

12.7 g (0.05 mole), N,N,N',N'-tetramethyl-4,4'-diaminodiphenylmethane and 11.5 g (0.45 mole) of 4,4-bis-(chloromethyl)-diphenyl are heated in 100 ml of methanol for 24 hours to reflux temperature.

The solvent is then distilled off and the residue is taken up in 150 ml of ether. The solution is stirred and the precipitate is collected by filtration and dried at 40° C., yielding a powder which dissolves in water to give a clear solution.

Yield: 23.7 g (98% of theory) of a reaction product containing recurring units of the formula

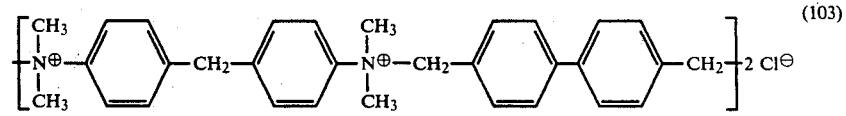

Viscosity: $\eta=0.54$ (25° C. in methanol, [dl/g]) Average molecular weight: 7900.

The viscosity in this Example and the subsequent Examples is the inherent viscosity. The values refer to solutions of 0.5% (g/v) in methanol. The average molecular weights have been determined from these viscosities.

Viscosity: $\eta=0.13$ (25° C. in methanol, [dl/g]) Average molecular weight: 1900

Manufacturing Direction 3

Following the procedure of Manufacturing Direction 1, equimolar amounts of 4,4'-bis-(chloromethyl)-diphenyl are reacted with diamines of the following formulae:

a. 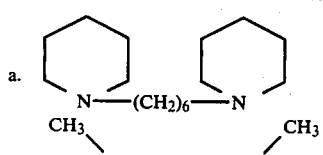  (104)

b. 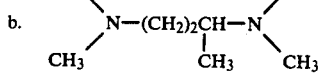  (105)

c. 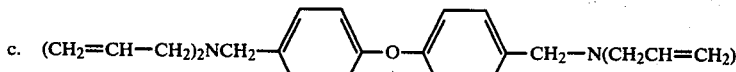  (106)

yielding reaction products containing recurring units of the formulae

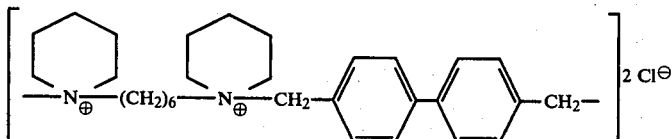 (107)

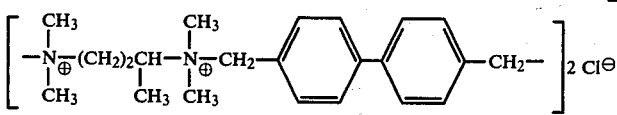 (108)

and

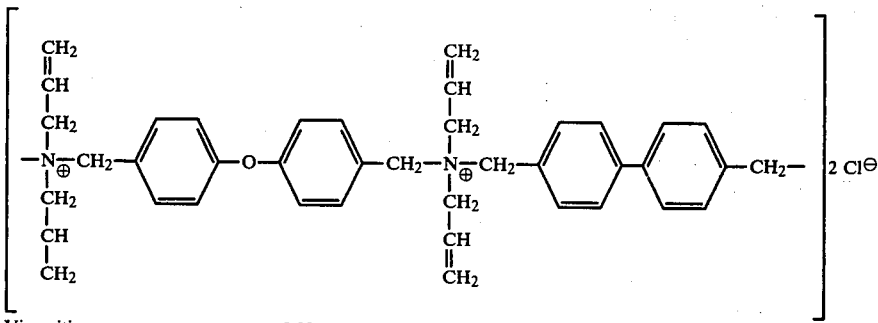 (109)

| Viscosities: 25° C. in methanol [dl/g] | a. η = 0.23 |
|---|---|
|  | b. η = 0.19 |
|  | c. η = 0.12 |
| Average molecular weights: | a. 3400 |
|  | b. 2800 |
|  | c. 1700 |

MANUFACTURING DIRECTION 4

(a) With stirring, 86.15 g (0.5 mole) of N,N,N'N'-tetramethyldiaminohexane and 125.5 g (0.5 mole) of 4,4'-bis-(chloromethyl)-diphenyl are heated in 300 ml of methanol to reflux temperature. A further amount of 200 ml of methanol is added to the reaction mixture, which becomes viscous with increasing reaction time. After 24 hours under reflux the reaction is complete and the solvent is distilled off, affording 212 g (100% of theory) of a reaction product which contains recurring units of the formula

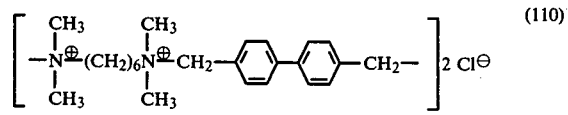 (110)

The product dissolves in water to give a clear solution. Viscosity: η=1.54 (25° C. in methanol, [dl/g]) Average molecular weight: 23,000

(b) 25.12 g (0.1 mole) of 4,4'-bis-(chloromethyl)-diphenyl are dissolved in 80 ml of acetone and the solution is heated to reflux temperature (56° C.). With stirring, a solution of 17.23 g (0.1 mole) of 1,6-bis-(dimethylamino)-hexane in 20 ml of acetone is added in the course of 1 minute. The reaction is exothermic and simultaneously a colourless precipitate begins to form. After 4 hours at reflux temperature the reaction is complete and the precipitate is collected by filtration and dried. Yield: 42.3 g (100% of theory) of a reaction product containing recurring units of the formula (110). The product is a white hygroscopic powder which dissolves in water to give a clear solution.

Viscosity: η=0.30 (25° C. in methanol, [dl/g]) Average molecular weight: 4400.

MANUFACTURING DIRECTION 5

(a) With stirring, 12.56 g (0.05 mole) of 4,4'-bis-(chloromethyl)-diphenyl and 13 g (0.1 mole) of 1,3-bis-(dimethylamino)-propane are heated for 30 hours to 60° C. The resulting viscous reaction mixture is suspended in 50 ml of water and clarified by filtration. The filtrate is concentrated to dryness, affording 16 g of a reaction product which contains recurring units of the formula

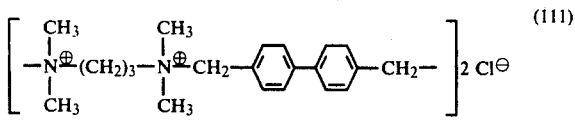

(111)

Yield: 62.2% of theory Viscosity: η=0.14 (25° C. in methanol, [dl/g]) Average molecular weight: 2000 The reaction products of 4,4'-bis-(chloromethyl)-diphenyl and the diamines listed in Table II are obtained in analogous manner using a solvent.

(1) The reaction products precipitate during the reaction. They are collected by filtration after completion of the reaction and dried.

(2) Sparingly soluble compound: chemical structure determined by elemental analysis, infra-red and NMR spectrum.

(3) 4,4'-Bis-(bromomethyl)-diphenyl was used.

(4) The quaternary product was extracted with water from the reaction mixture.

(5) 4,4'-bis-(iodomethyl)-diphenyl was used.

(6) The reaction product is subsequently quaternised with ethyl chloroacetate.

Table II

| Manufacturing Direction | Diamine | Reaction conditions | Yield (% of theory) | Viscosity η | Average mol. wt. |
|---|---|---|---|---|---|
| b | $(CH_3)_2N(CH_2)_6N(CH_3)_2$ | 1 hr., acetone, 56° C. | 100 | 0.26 | 3800 |
| c | $(CH_3)_2N(CH_2)_6N(CH_3)_2$ | 4 hrs., acetone, 56° C. | 100 | 0.30 | 4400 |
| d | $(CH_3)_2N(CH_2)_6N(CH_3)_2$ | 4 hrs., acetone, 56° C.[1] | 93.3 | 0.26 | 3800 |
| e | $(CH_3)_2N(CH_2)_6N(CH_3)_2$ | 4 hrs., acetone, 20° C. | 98.2 | 0.31 | 4500 |
| f | $(CH_3)_2N(CH_2)_{12}N(CH_3)_2$ | 24 hrs., methanol 63° C. | 100 | 1.54 | 23000 |
| g | $(CH_3)_2N(CH_2)_{12}N(CH_3)_2$ | 24 hrs., methanol, acetone, v/v 1:1, 60° C. | 49.4 | 0.11 | 1600 |

[1]Addition of the diamine in the course of 1 ½ hours.

MANUFACTURING DIRECTION 6

The procedure of Manufacturing Direction 4 is repeated using equivalent amounts of 4,4'-bis-(chloromethyl)-diphenyl and one of the following diamines.

The reaction products of Manufacturing Directions 6a to 6g can be illustrated by the following structural formulae (recurring units):

Table III

| Manufacturing Direction | Diamine | Reaction conditions | Yield (% of theory) | Viscosity η | Average mol. wt. |
|---|---|---|---|---|---|
| (a) | morpholine-N-(CH₂)₂-N-morpholine | 24 hrs., methanol, 60° C. | 25 | 0.06 | 900 |
| (b) | piperazine (HN-NH) | 27 hrs., methanol, 60° C.[6] | 100 | 0.04 | 600 |
| (c) | $(CH_3)_2N$-cyclohexyl-C(CH_3)_2-cyclohexyl-$N(CH_3)_2$ | 27 hrs., methanol, 60° C. | 100 | 0.35 | 5100 |
| (d) | pyrazine | 4 hrs., acetone, 56° C. | 71 | 0.05 | 700[1] |
| (e) | 4,4'-bipyridyl | 4 hrs., acetonitrile, 65°–70° C. | 100 | — | —[1][2][3] |
| (f) | $(CH_3CHCH_2)_2N(CH_2)_6N(CH_2CHCH_3)_2$, OH, OH | 56 hrs., methyl ethyl ketone, 80° C. | 7 | 0.08 | 1100[4][5] |
| (g) | $CH_3$-N(CH₃)-CH₂-C₆H₄-C₆H₄-CH₂-N(CH₃)-$CH_3$ | 24 hrs., methanol 60° C. | 100 | 0.51 | 7500 |

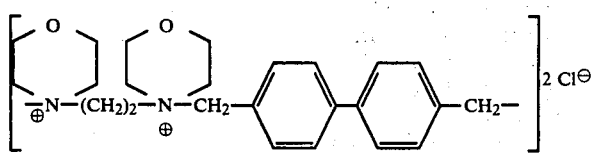
(112)

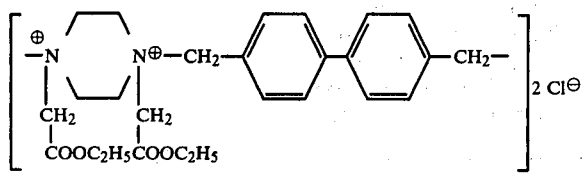
(113)

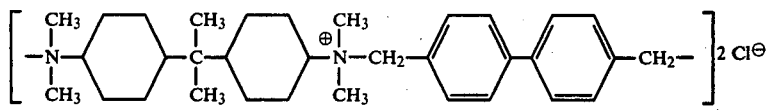
(114)

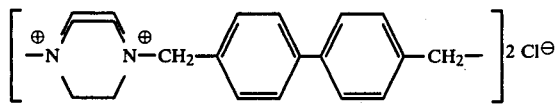
(115)

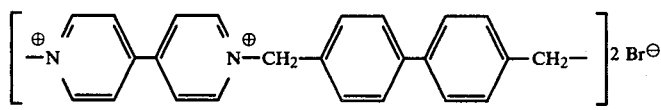
(116)

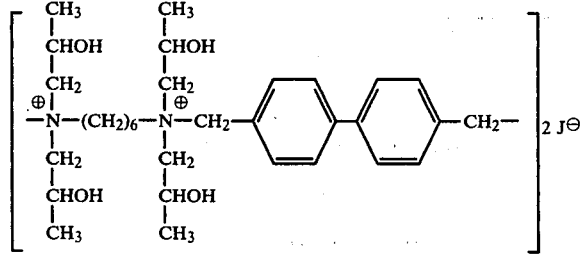
(117)

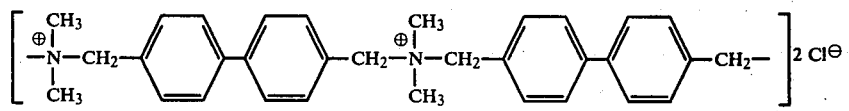
(118)

MANUFACTURING DIRECTION 7

35.2 g (0.1 mole) of the diamine of the formula

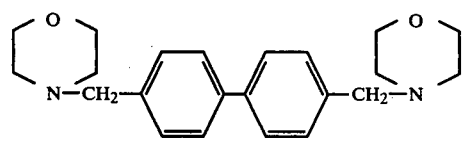
(119)

and 24.4 g (0.1 mole) of 1,6-dibromohexane are heated in 300 ml of methanol for 24 hours to reflux temperature. The solvent is then distilled off and the residue is taken up in ether in order to remove the water-insoluble constituents. A water-soluble reaction product containing recurring units of the formula (120)

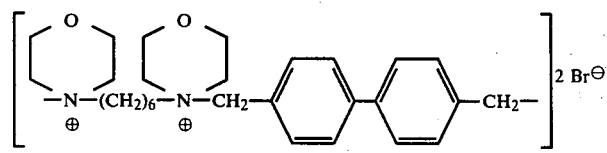

is obtained.

Yield: 30% of theory
Viscosity: $\eta = 0.06$ (20° C. in methanol, [dl/g])
Average molecular weight: 900

MANUFACTURING DIRECTION 8

Equimolar amounts of a diamine of the formula

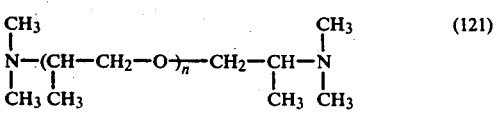
(121)

and 4,4'-bis-(chloromethyl)-diphenyl are reacted in methanol for 24 hours at reflux temperature. The solvent is removed, yielding reaction products containing recurring units of the formula

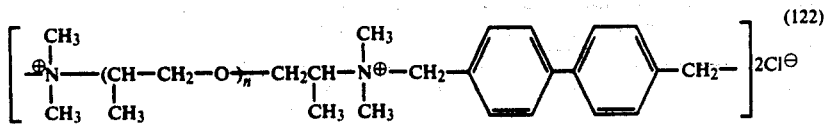

Table IV

| Manufacturing Direction | n | Yield of theory (%) | Viscosity η | Average mol. wt. |
|---|---|---|---|---|
| a | 2.6 | 100 | 0.30 | 4400 |
| b | 5.6 | 100 | 0.21 | 3100 |
| c | 33.1 | 100 | 0.68 | 10000 |

MANUFACTURING DIRECTION 9

Equimolar amounts of the dichlorides listed in Table 5 and 4,4'-bis-(dimethylaminomethyl)-diphenyl are heated in acetone for 24 hours to reflux temperature. The reaction product precipitates in the course of the reaction. When the reaction is complete, the reaction mixture is cooled and the precipitated product is collected by filtration and dried.

Table V

| Manufacturing Direction | Dichloride | Yield of theory (%) | Viscosity η | Average mol. wt. |
|---|---|---|---|---|
| (a) | Cl—CH₂—(o-C₆H₄)—CH₂—Cl | 88.3 | 0.36 | 5300 |
| (b) | Cl—CH₂—(p-C₆H₄)—CH₂—Cl | 94.3 | 0.29 | 4300 |
| (c) | Cl—CH₂—(naphthyl)—CH₂—Cl (ratio of the 1,4:1,5 isomers is 40:60) | 100 | 0.19 | 2800 |
| (d) | Cl—CH₂—(tetrahydronaphthyl)—CH₂—Cl | 100 | 0.22 | 3200 |

Table V-continued

| Manufacturing Direction | Dichloride | Yield of theory (%) | Viscosity $\eta$ | Average mol. wt. |
|---|---|---|---|---|
| (e) | Cl—CH$_2$—C(=O)—CH$_2$—Cl[1] | 70.5 | 0.07 | 1000 |

[1] Reaction conditions: 24 hours in acetone at room temperature (20° to 25° C.).

The reaction products of Manufacturing Directions 9a to 9e can be illustrated by the following structural formulae (recurring units):

(123) 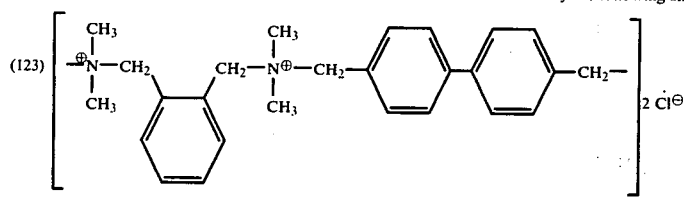

(124) 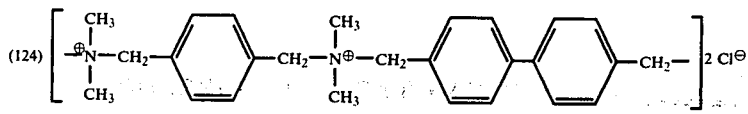

(125) 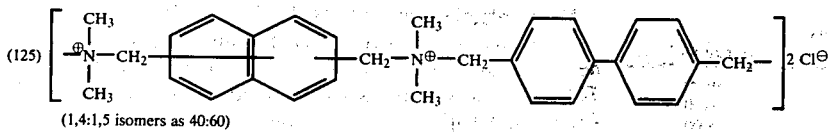
(1,4:1,5 isomers as 40:60)

(126) 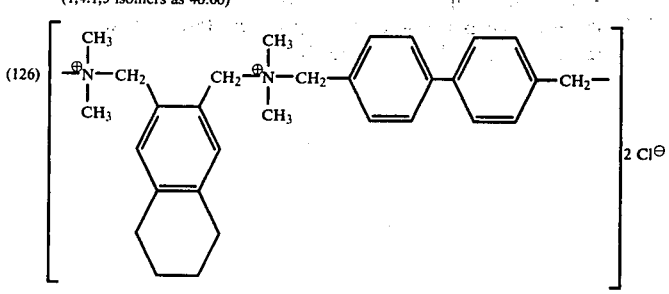

(127) 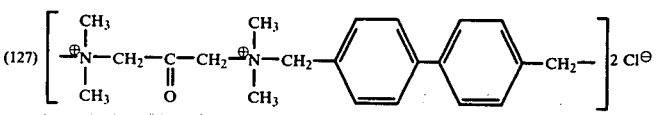

MANUFACTURING DIRECTION 10

Equimolar amounts of the diamine of the formula

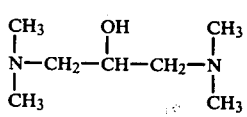 (128)

and 4,4'-bis-(chloromethyl)-diphenyl and 1.1 equivalents of sodium iodide are heated in acetone for 48 hours under reflux (56° C.). The reaction solution is then filtered. The solvent is distilled off, affording as residue a colourless reaction product containing recurring units of the formula

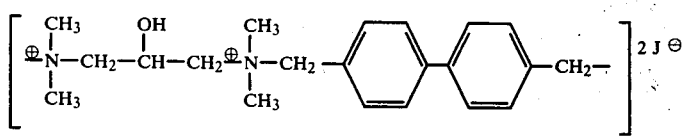

Yield: 72.7% of theory. The iodide can be converted into the corresponding chloride by reaction with freshly precipitated silver chloride (24 hours in methanol at 64° C., then filter, remove the methanol and dry the residual product).

Viscosity: $\eta$ 0.38 (25° C. in methanol [dl/g]) Average molecular weight: 4100.

MANUFACTURING DIRECTION 11

Equimolar amounts of the diamine of the formula

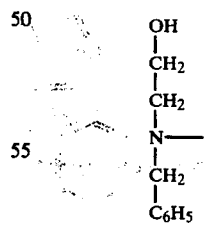 (130)

(129)

and 4,4'-bis-(chloromethyl)-diphenyl are heated in acetone for 24 hours to reflux temperature (56° C.). When the reaction is complete, the solvent is distilled off and the residue extracted with hot water. A colourless reaction product which contains recurring units of the formula

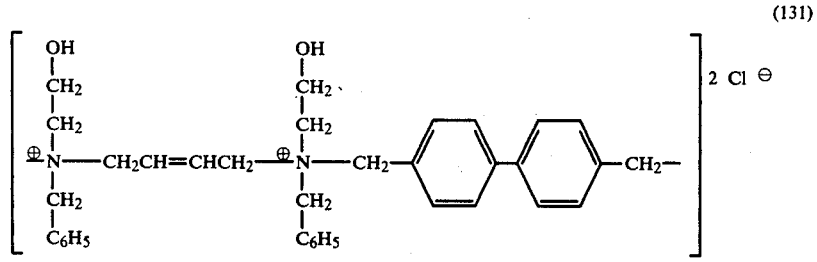
(131)

is obtained from the aqueous solution after removal of the water.

Yield: 47.7% of theory Viscosity: η=0.1 (25° C. in methanol, [dl/g]) Average molecular weight: 1400. The infra-red spectrum (KBr) shows absorption bands at 3310, 3050, 2960, 2740, 2620, 1970, 1925, 1835, 1660, 1615, 1590, 1505, 1460, 1220, 1090, 1055, 1010, 960, 930, 815, 755, 705 and 665 cm⁻¹.

MANUFACTURING DIRECTION 12

Equimolar amounts of the dichloro compound of the formula

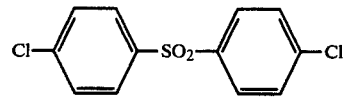
(132)

and 4,4'-bis-(dimethylaminomethyl)-diphenyl are reacted as described in Manufacturing Direction 9, yielding a reaction product which contains recurring units of the formula

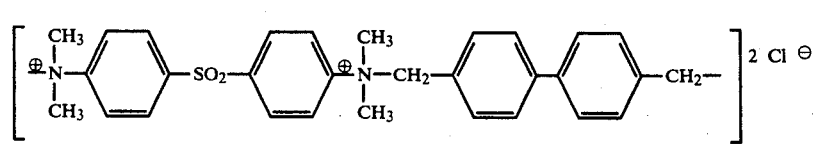
(133)

Yield: 23% of theory.

The product is insufficiently soluble in methanol, so that viscosity values could not be determined in this solvent. The infra-red spectrum (KBr) shows absorption bands at 3470, 3280, 1615, 1565, 1465, 1375, 1240, 1120, 1075, 1040, 995, 970, 825, 735, 600, 575, 505, 475 and 420 cm⁻¹.

Manufacturing Direction 13

25.5 g (0.1 mole) of 4,4'-bis-(chloromethyl)-diphenyl and 8.88 g (0.1 mole) of piperazine together with 11.7 g of sodium carbonate are taken up in 200 ml of benzene and the solution is heated, with stirring, to 60° C. When the reaction is complete, the reaction mixture is cooled to room temperature (20°–25° C.) and filtered. The residue is washed with 400 ml of water and then dried, affording 14.7 g (55.6% of theory) of a compound which contains recurring units of the formula $$\left[ -N\diagup\diagdown N-CH_2-\phenyl-\phenyl-CH_2- \right]$$
(134)

With stirring, 3.97 g (0.015 mole) of this reaction product and 13.04 g (0.12 mole) of methyl chloroacetate are heated for 15 hours at 80°–90° C. When the reaction is complete, the reaction mixture is cooled and the reaction product is extracted with 100 ml of water. The aqueous solution is concentrated, affording 101 g (14% of theory) of a reaction product which contains recurring units of the formula $$\left[ \begin{array}{c} {}^{\oplus}N\diagup\diagdown N^{\oplus}\text{-}CH_2\text{-}\phenyl\text{-}\phenyl\text{-}CH_2\text{-} \\ | \quad\quad\quad | \\ CH_2COOCH_3 \\ CH_2COOCH_3 \end{array} \right] 2\,Cl^{\ominus}$$
(135)

Viscosity: η=0.17 (25° C. in methanol [dl/g]) Average molecular weight: 2500.

MANUFACTURING DIRECTION 14

50.23 g (0.2 mole) of 4,4'-bis-(chloromethyl)-diphenyl and 26.05 g (0.5 mole) of N,N,N',N'-tetramethyl-1,3-diaminopropane are heated for 24 hours in 200 ml of water to 95° C. The reaction mixture obtained on completion of the reaction and cooling to room temperature (20°–25° C.) can be further diluted with water, for example with 100 ml, and used direct for the different application purposes. The reaction product contains the recurring units of the formula

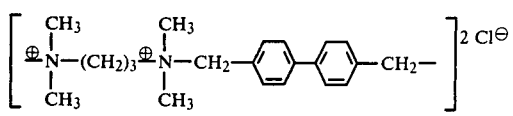
(136)

Solids content of the aqueous solution (after dilution with water):
calculated: 21.6% (g/g) found: 22.6% chlorine content (titration): calculated (complete quaternisation): 4.0% found: 3.9%.

The reaction product of the formula (136) can be obtained in substance by removal of the water or precipitation with acetone.

Yield: 100% of theory
Viscosity: $\eta = 0.42$ (25° C. in methanol [dl/g] Instead of using water as solvent, it is also possible to use mixtures of water with other solvents, especially those which are water-miscible, for example isopropanol, and thus improve the homogeneity of the reaction mixture. Analogous products with average molecular weights of 8800 to 15,200 can be obtained in this way.

MANUFACTURING DIRECTION 15

Equimolar amounts of the compound of the formula

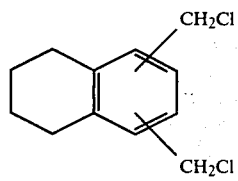
(137)

2,3- or 1,4-isomers and N,N,N',N'-tetramethyldiaminohexane are reacted in accordance with the procedure of Manufacturing Direction 14, affording in quantitative yield a polymeric quaternary ammonium salt which contains recurring units of the formula

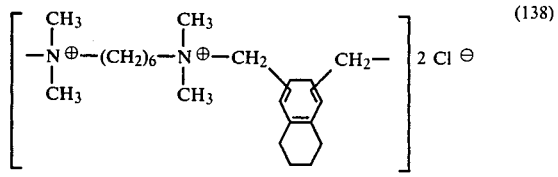
(138)

Viscosity: $\eta = 0.32$ (25° C. in methanol, [dl/g])
Average molecular weight: 4700.

EXAMPLE 1

(a) Conditioning Shampoo
Composition:
1.5 parts of the reaction product of Manufacturing Direction (1g)
14.3 parts of 2-lauryl-1-(sodium carboxymethyl)-1-(sodium 2-carboxymethyloxy)-2-hydroxyimidazoline (70%)
2 parts of lauric diethanolamide, made up to 100 parts with deionised water, preservative and perfume.
The pH value of the composition is 6–8, adjusted with citric acid.

This shampoo is applied to the hair in known manner and a thick, stable foam is formed. The hair, which is well rinsed with water after shampooing, is easy to comb. After drying, it is distinguished by fullness, silkiness and natural lustre. Instead of using 14.3 parts of the above hydroxyimidazoline, it is also possible to use 10 parts of sodium laurylsarcosinate with equally good results. Compositions containing 0.5 or 1 part of the reaction product of Manufacturing Direction (1g) also have a good action.

(b) Setting shampoo

A shampoo of the same composition as in (a) is used. The shampooed hair is rinsed, then wound on rollers to form curls and afterwards dried in the air or with a hand-drier. After the rollers have been taken out, the hair can be very easily combed and brushed, and it has fullness, silkiness and natural lustre. The resulting set has very good retention of shape, especially in a moist climate.

By using this so-called "setting shampoo", it is thus possible to obtain directly after shampooing, and without the application of a setting aid, hair which is easily combed and which makes it possible to produce good hairstyles.

(c) If the setting shampoo of (b) contains a reaction product with recurring units of the formulae

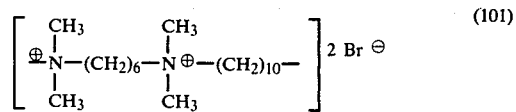
(101)

or

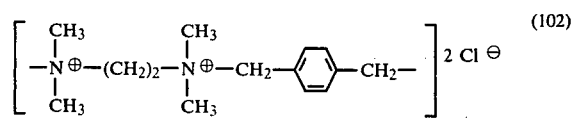
(102)

according to German Offenlegungsschrift No. 2,521,960, then the resulting set has only an insufficient retention of shape (curl retention), especially in a moist climate.

| Preparations containing the reaction product of | Curl retention |
|---|---|
| Manufacturing Direction (1g) | 64% |
| formula (101) | 22% |
| formula (102) | 25% |

EXAMPLE 2

Setting Lotion

Composition:

1 part of the reaction product of Manufacturing Direction (1e) 15 parts of ethyl alcohol, made up to 100 parts with deionised water, preservative and perfume. The pH of the composition is 5–7, adjusted with lactic acid or aqueous ammonium hydroxide solution.

The hair is treated with this solution at room temperature, set and dried. The resulting curls have extremely good retention of shape, especially in a moist climate (curl retention 74%). The hair is easy to comb, the handle is pleasing and the tendency of the hair to "fly" on combing is markedly reduced. The hair remains elastic and full, the film does not flake and can be easily washed off.

If the hair is treated in the same manner with compositions which contain the reaction products of the formulae (101) or (102) according to German Offenlegungsschrift No. 2,521,961, the set has poor retention of shape (curl retention), especially in a moist climate.

EXAMPLE 3

Conditioning pre- and after-rinse

Before or after shampooing, the hair is treated with a solution consisting of 1 part of the reaction product of Manufacturing Direction (1e), and made up to 100 parts with deionised water, preservative, perfume, tint, and lactic acid or aqueous ammonium hydroxide solution (pH of the solution: 5–7), then rinsed out after 3 to 5 minutes. The treated hair is particularly easy to care for and little susceptible to harmful influences.

EXAMPLE 4

Setting Lotion

Treatment solutions are prepared from 1 part of each of the reaction products of Manufacturing Directions (2), (6e), (8a) and (9a), 20 parts of ethanol and 79 parts of distilled water.

The solutions have the following pH values:

| 1% solution of the reaction product of Manufacturing Direction | pH value |
| --- | --- |
| (I) 6c | 3.45 |
| (II) 6e | 5.65 |
| (III) 8a | 9.85 |
| (IV) 9a | 8.20 |

Strands of hair are treated with these solutions, set and dried. All the strands exhibit good curl retention. The hair is lustrous and soft and has good curl retention. It is also easy to comb and wash. The curl retention values are 50, 43, 34 and 42% respectively for the strands of hair treated with the solutions I to IV.

What is claimed is:

1. Hair-care compositions in the form of aqueous, alcoholic or aqueous alcoholic solutions, creams, gels, emulsions, or of aerosols which optionally contain a propellant, said compositions containing 0.01 to 10 percent by weight of at least one polymeric quaternary ammonium salt which contains cationic units of the formula

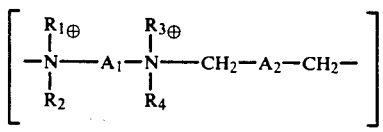

wherein $R_1$, $R_2$, $R_3$ and $R_4$ are the same or different and represent unsubstituted or substituted alkyl, cycloalkyl or alkenyl of at most 20 carbon atoms, aryl or aralkyl, or ($R_1$ and $R_2$) and/or ($R_3$ and $R_4$) together with the nitrogen atom to which they are bonded, form an unsubstituted or substituted heterocyclic ring containing 3 to 6 ring members, $A_1$ represents —$(CH_2)_m$—, wherein m is an integer from 1 to 20, which can be interrupted by at least one —S—,

or —CH=CH— group or substituted by at least one member selected from the group consisting of hydroxyl, halogen, nitrile, alkyl, hydroxy-alkyl, alkoxy, carboxyl or carbalkoxy or by at least one unsubstituted or substituted aryl or aralkyl radical, or represents polyoxyalkylene, or a radical of the formulae

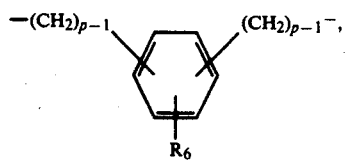

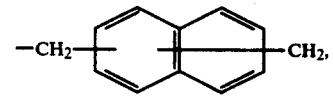

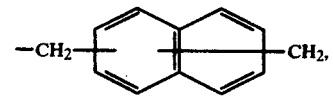

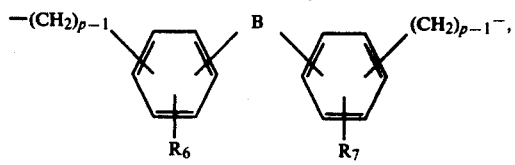

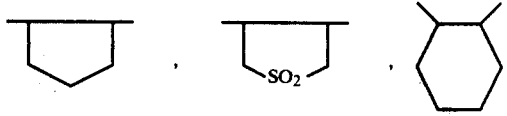

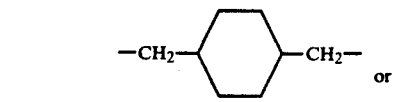

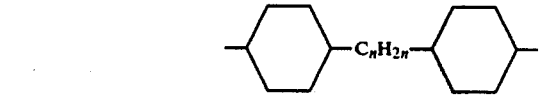

or together with the nitrogen atoms and at least one of the substituents bonded thereto $A_1$ represents a radical of the formulae

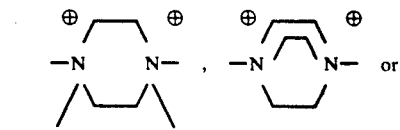

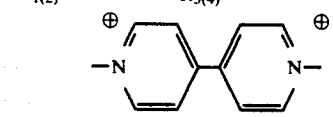

$R_6$ and $R_7$ represent hydrogen, alkyl, hydroxyl or haloalkyl of 1 to 4 carbon atoms, hydroxyl, halogen, carboxyl, carbalkoxy or phenyl, B represents the direct bond, $-O-, -\underset{\underset{O}{\|}}{C}-, -S-, -SO_2-$ or unsubstituted or substituted alkylene,
n is an integer from 1 to 6,
p is an integer from 1 to 3, and
$A_2$ represents a radical of the formula

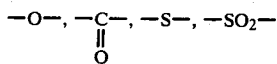

2. Compositions according to claim 1, wherein the cationic units of the polymeric quaternary ammonium salts have the formula

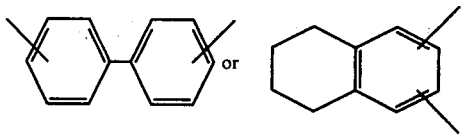

wherein $R_9$, $R_{10}$, $R_{11}$ and $R_{12}$ are the same or different and represent alkenyl of 2 to 20 carbon atoms, cycloalkyl of 5 to 6 carbon atoms; alkyl, hydroxyalkyl, cyanoalkyl, alkoxyalkyl, alkylthioalkyl and alkylcarbonylalkyl of 1 to 10 carbon atoms; arylcarbonylalkyl, alkylsulphonylalkyl and arylsulphonylalkyl, each containing 1 to 4 carbon atoms in the alkyl moiety; alkylcarboxylic acid containing 1 to 4 carbon atoms in the alkyl moiety; carbalkoxyalkyl and di(carbalkoxy)alkyl, each containing 1 to 4 carbon atoms in the alkoxy and alkyl moieties; carboxamidoalkyl containing 1 to 10 carbon atoms in the alkyl moiety and which can be N-substituted by lower alkyl or aryl; or represent phenyl or benzyl which are unsubstituted or substituted by hydroxyl, cyano, halogen and carboxyl; alkyl, hydroxyalkyl, cyanoalkyl, alkoxy and alkylthio of 1 to 4 carbon atoms; alkoxyalkyl, carbalkoxyalkyl and di(carbalkoxy)alkyl, each containing 1 to 4 carbon atoms in the alkyl and alkoxy moieties; alkylcarboxylic acid containing 1 to 4 carbon atoms in the alkyl moiety; or carboxamidoalkyl containing 1 to 4 carbon atoms in the alkyl moiety and which is unsubstituted or N-substituted by lower alkyl; or ($R_9$ and $R_{10}$) and/or ($R_{11}$ and $R_{12}$), together with the nitrogen atom to which they are bonded, form an unsubstituted or substituted heterocyclic ring containing 5 or 6 ring members, $A_3$ represents $-(CH_2)_m-$, wherein m is an integer from 1 to 20, which can be interrupted by at least one

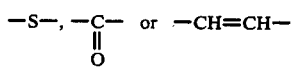

group or substituted by at least one member selected from the group consisting of hydroxyl, chlorine, nitrile or alkyl, alkoxy or hydroxyalkyl of 1 to 4 carbon atoms, carboxyl or carbalkoxy containing 1 to 20, preferably 1 to 4, carbon atoms in the alkoxy moiety, or by unsubstituted or substituted phenyl or benzyl radicals; or $A_3$ also represents a group of the formula

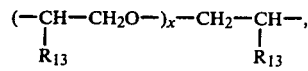

a radical of the formulae

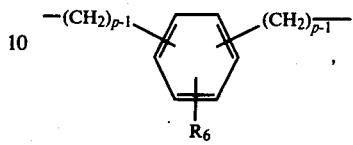

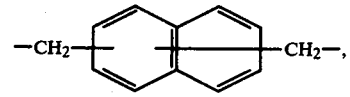

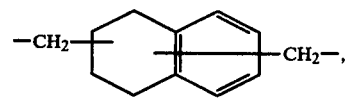

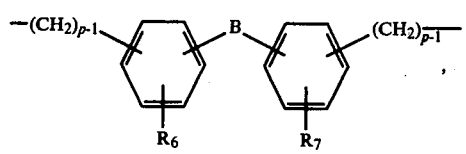

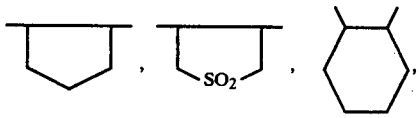

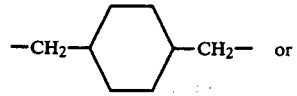

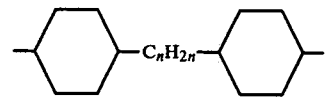

or together with the nitrogen atoms and at least one of the substituents which are bonded thereto is a radical of the formulae

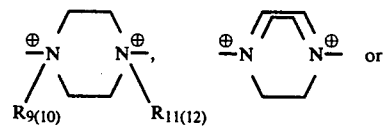

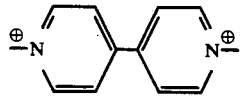

$R_{13}$ represents hydrogen or methyl and x is at least 1, and $A_2$, $R_6$, $R_7$, B, n and p are as defined in claim 1.

3. Compositions according to claim 2, wherein the cationic units of the polymeric quaternary ammonium salts have the formula

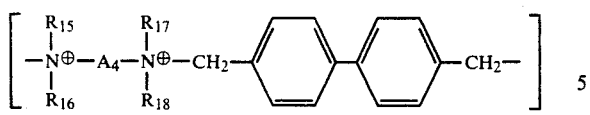

wherein

R$_{15}$, R$_{16}$, R$_{17}$ and R$_{18}$ are the same or different and represent alkyl, hydroxyalkyl, alkoxyalkyl, alkylthioalkyl and cyanoalkyl of 1 to 4 carbon atoms; cyclopentyl, cyclohexyl, alkenyl of 2 to 4 carbon atoms, CH$_3$COCH$_2$—, HOOC—CH$_2$—, CH$_3$OOCCH$_2$—, H$_5$C$_2$OOCCH$_2$—, (CH$_3$OOC)$_2$CH—, H$_2$NCOCH$_2$—,

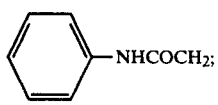

or represent phenyl or benzyl which are unsubstituted or substituted by hydroxyl, amino, cyano, fluorine, chlorine, bromine, alkyl, hydroxyalkyl, cyanoalkyl, alkoxy and alkylthio, each containing 1 or 2 carbon atoms, alkoxyalkyl, carbalkoxyalkyl and di(carboxyalkyl) containing 1 or 2 carbon atoms in the alkyl and alkoxy moiety —CH$_2$COOH, —(CH$_2$)$_2$COOH, carboxamidoalkyl with 1 or 2 carbon atoms on the alkyl moiety and optionally N-substituted by lower alkyl, or (R$_{15}$ and R$_{16}$) and/or (R$_{17}$ and R$_{18}$) together with the nitrogen atom to which they are bonded form a heterocyclic ring of the formulae

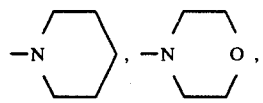

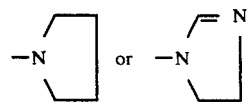

wherein

A$_4$ represents —(CH$_2$)$_{m1}$, wherein m$_1$ is an integer from 1 to 12,

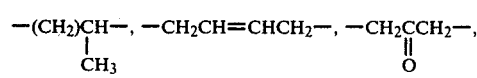

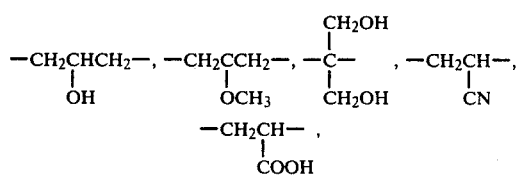

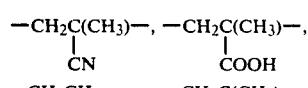

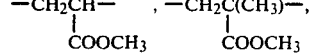

-continued

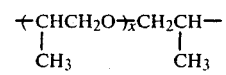

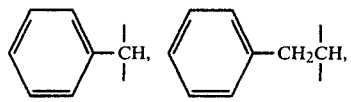

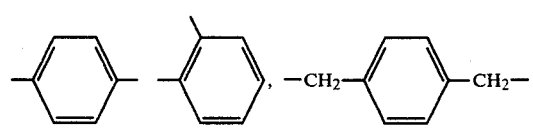

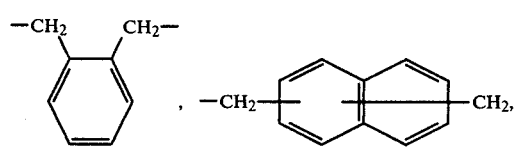

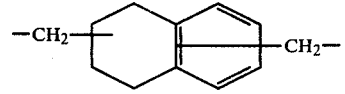

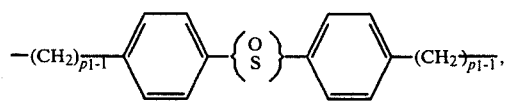

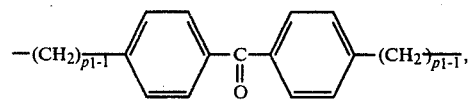

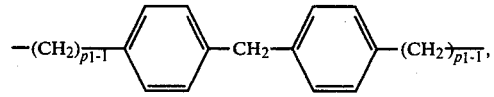

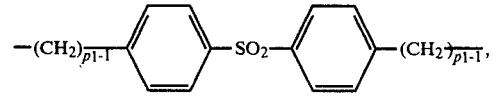

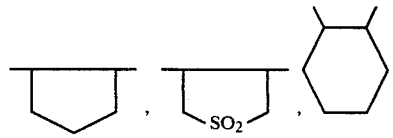

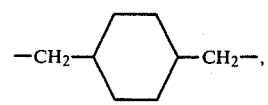

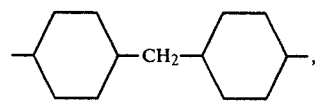

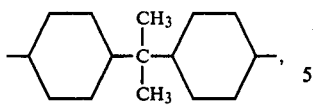

wherein x is at least 1 and $p_1$ is 1 or 2 or together with the nitrogen atoms and at least one of the substitutents bonded thereto $A_4$ represents a radical of the formulae

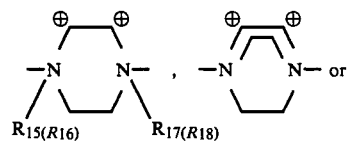

4. Compositions according to claim 3, wherein $R_{15}$, $R_{16}$, $R_{17}$ and $R_{18}$ are the same or different and represent alkyl or hydroxyalkyl of 1 to 4 carbon atoms, alkenyl of 2 or 4 carbon atoms, $CH_3OOCCH_2-$, $C_2H_5OOCCH_2-$ or benzyl or ($R_{15}$ and $R_{16}$) and/or ($R_{17}$ and $R_{18}$) together with the nitrogen atom to which they are bonded form a heterocyclic ring of the formula

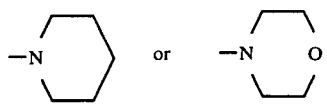

and $A_4$ represents $-(CH_2)_{m1}-$, wherein $m_1$ is an integer from 1 to 12,

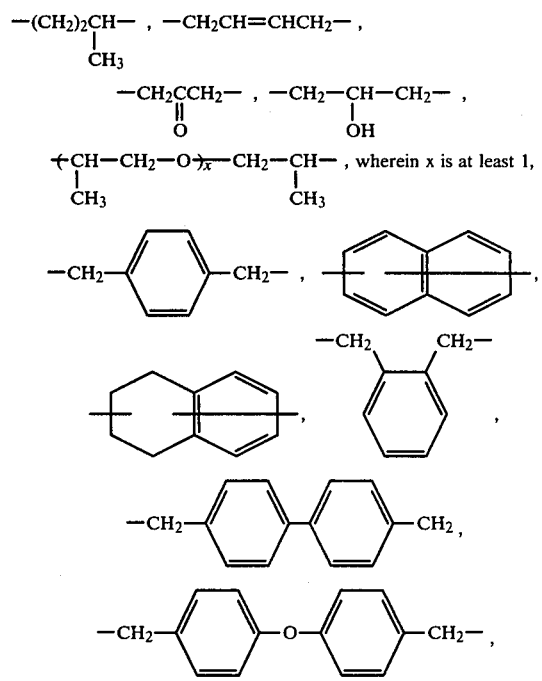

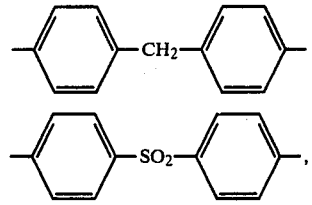

or together with the nitrogen atoms and at least one of the substituents bonded thereto $A_4$ represents a radical of the formulae

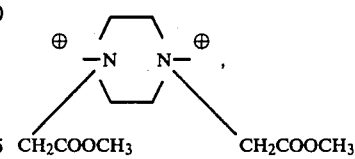

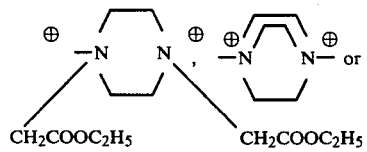

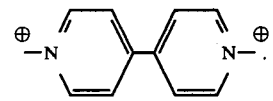

5. Compositions according to claim 4, wherein $A_4$ represents $-(CH_2)_{3-6}$, $-(CH(CH_3)CH_2O)_{2,6}CH_2CH(CH_3)-$

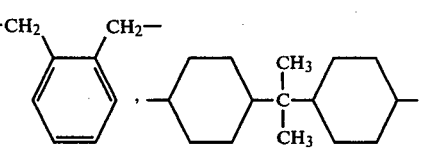

or together with the nitrogens and both substituents bonded thereto represents the radical of the formula

6. Compositions according to claim 3, wherein the recurring units of the polymeric quaternary ammonium salts have the formula

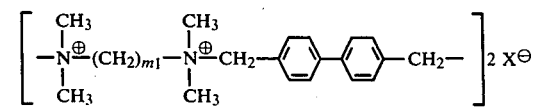

wherein $m_1$ is an integer from 1 to 12 and X represents halogen.

7. Compositions according to claim 6, wherein the recurring units of the polymeric quaternary ammonium salts have the formula

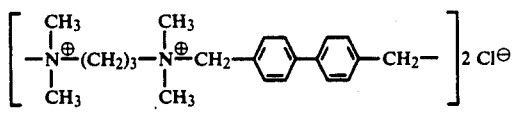

8. Compositions according to claim 6, wherein the recurring units of the polymeric quaternary ammonium salts have the formula

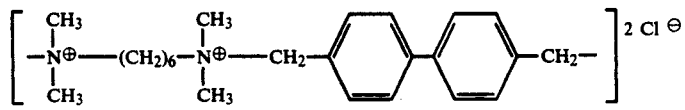

9. Compositions according to claim 6, wherein the recurring units of the polymeric quaternary ammonium salts have the formula

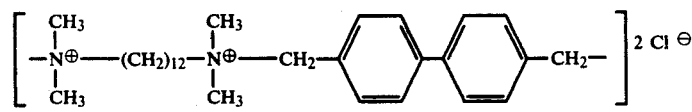

10. Cosmetic compositions according to claim 1, which are in the form of hair-rinses, hair-tints, hair-lacquers, pre-shampoo hair conditioners, hair-tonics, setting lotions, hairsprays, hair-creams, hair-gels, hair-oils, hair-pomades or brilliantines.

11. Cosmetic compositions according to claim 1 which are used as shampoos.

12. Cosmetic compositions according to claim 11 which are used as setting shampoos.

13. A method of treating human hair which comprises applying thereto at least one cosmetic composition according to any one of claims 1 to 12.

14. A method according to claim 13 wherein the cosmetic composition is a shampoo.

15. A method according to claim 14 which comprises washing human hair with the shampoo and rinsing it, and, directly afterwards winding the hair on rollers to form curls and drying it.

* * * * *